United States Patent [19]

Finch, Jr. et al.

[11] Patent Number: 5,807,356
[45] Date of Patent: Sep. 15, 1998

[54] CATHETER WITH VALVE

[75] Inventors: Charles David Finch, Jr., Clinton; Hendrik Klaas Kuiper, Edwards, both of Miss.

[73] Assignee: Vasca, Inc., Topsfield, Mass.

[21] Appl. No.: 539,105

[22] Filed: Oct. 4, 1995

Related U.S. Application Data

[63] Continuation-in-part of Ser. No. 183,151, Jan. 18, 1994, Pat. No. 5,562,617.

[51] Int. Cl.$^6$ .................................................. A61M 25/00
[52] U.S. Cl. ............................. 604/284; 604/4; 604/247; 604/264; 604/282
[58] Field of Search ............................ 604/4, 9, 83, 247, 604/264, 280, 282, 284

[56] References Cited

U.S. PATENT DOCUMENTS

| | | | |
|---|---|---|---|
| 274,447 | 3/1883 | Kennish . | |
| 3,331,371 | 7/1967 | Rocchi et al. | 128/349 |
| 3,516,408 | 6/1970 | Montanti | 128/214 |
| 3,699,956 | 10/1972 | Kitrilakis et al. | 128/348 |
| 3,826,257 | 7/1974 | Buselmeier | 128/214 R |
| 3,888,249 | 6/1975 | Spencer | 128/214 |
| 4,108,173 | 8/1978 | Silvenko et al. | 128/214 |
| 4,256,102 | 3/1981 | Monaco | 128/213 |
| 4,400,169 | 8/1983 | Stephen | 604/49 |
| 4,405,305 | 9/1983 | Stephen et al. | 604/49 |
| 4,417,888 | 11/1983 | Cosentino et al. | 604/175 |
| 4,421,507 | 12/1983 | Bokros | 604/52 |
| 4,428,364 | 1/1984 | Bartolo | 128/1 |
| 4,484,912 | 11/1984 | Raible | 604/175 |
| 4,496,350 | 1/1985 | Consentino | 604/175 |
| 4,543,088 | 9/1985 | Bootman et al. | 604/93 |
| 4,549,879 | 10/1985 | Groshong et al. | 604/247 |
| 4,634,422 | 1/1987 | Kantrowitz et al. | 604/49 |
| 4,638,803 | 1/1987 | Rand | 128/325 |
| 4,639,247 | 1/1987 | Bokros | 604/175 |
| 4,657,536 | 4/1987 | Dorman | 604/247 |
| 4,671,796 | 6/1987 | Groshong et al. | 604/247 |
| 4,673,394 | 6/1987 | Fenton, Jr. et al. | 604/175 |
| 4,685,905 | 8/1987 | Jeanneret nee Aab | 604/247 |
| 4,692,146 | 9/1987 | Hilger | 604/93 |
| 4,695,273 | 9/1987 | Brown | 604/173 |
| 4,701,166 | 10/1987 | Groshong et al. | 604/247 |
| 4,704,103 | 11/1987 | Stöber et al. | 604/175 |
| 4,705,501 | 11/1987 | Wigness et al. | 604/43 |
| 4,759,752 | 7/1988 | Stöber | 604/247 |
| 4,772,270 | 9/1988 | Wiita et al. | 604/175 |
| 4,802,885 | 2/1989 | Weeks et al. | 604/93 |

(List continued on next page.)

FOREIGN PATENT DOCUMENTS 228532   1/1983   European Pat. Off. .

OTHER PUBLICATIONS

Trans. of Amer. Soc. for Art. Int. Organs vol. 28, 14 Apr. 1982: 16 Apr. 1982; Chicago, Ill.; pp. 54–57.

*Primary Examiner*—Wynn Wood Coggins
*Assistant Examiner*—Deborah Blyveis
*Attorney, Agent, or Firm*—Townsend and Townsend and Crew LLP

[57] ABSTRACT

A catheter with valve for implantation in a vascular structure of a living being. The catheter is in the general shape of a "T" with the top of the "T" implanted within the lumen of a vascular structure, and the leg of the "T" extending out of the vascular structure through an incision in the vascular structure. The lumen of the implanted portion of the catheter completely occupies the lumen of the vascular structure, causing all blood flow through the vascular structure to be directed through the implanted portion of the catheter. A valve is placed in the wall of the implanted portion of the catheter which opens into the lumen of the leg of the "T" of the catheter upon application of sufficient differential pressure between the lumens of the two portions of the catheter. The leg of the "T" is connected to the side wall of the implanted portion of the catheter at an angle, such that the axis of the lumen of the leg of the "T" intersects the axis of the lumen of the implanted portion of the catheter at approximately a 45 degree angle.

22 Claims, 2 Drawing Sheets

U.S. PATENT DOCUMENTS

| | | | |
|---|---|---|---|
| 4,840,190 | 6/1989 | Sasaki | 128/897 |
| 4,846,806 | 7/1989 | Wigness et al. | 604/175 |
| 4,857,053 | 8/1989 | Dalton | 604/93 |
| 4,892,518 | 1/1990 | Cupp et al. | 604/93 |
| 4,973,319 | 11/1990 | Melsky | 604/247 |
| 5,030,210 | 7/1991 | Alchas | 604/247 |
| 5,041,098 | 8/1991 | Loiterman et al. | 604/175 |
| 5,041,101 | 8/1991 | Seder et al. | 604/284 |
| 5,053,013 | 10/1991 | Ensminger et al. | 604/167 |
| 5,057,084 | 10/1991 | Ensminger et al. | 604/167 |
| 5,090,954 | 2/1992 | Geary | 604/29 |
| 5,100,392 | 3/1992 | Orth et al. | 604/175 |
| 5,102,389 | 4/1992 | Hausser | 604/93 |
| 5,112,301 | 5/1992 | Fenton, Jr. et al. | 604/30 |
| 5,137,529 | 8/1992 | Watson et al. | 604/891.1 |
| 5,156,600 | 10/1992 | Young | 604/247 |
| 5,167,638 | 12/1992 | Felix et al. | 604/175 |
| 5,176,627 | 1/1993 | Watson | 604/8 |
| 5,176,653 | 1/1993 | Metais | 604/167 |
| 5,180,365 | 1/1993 | Ensminger et al. | 604/93 |
| 5,224,938 | 7/1993 | Fenton, Jr. | 604/247 |
| 5,263,930 | 11/1993 | Ensminger | 604/93 |
| 5,290,263 | 3/1994 | Wigness et al. | 604/247 |
| 5,306,255 | 4/1994 | Haindl | 604/175 |
| 5,318,545 | 6/1994 | Tucker | 604/244 |
| 5,324,518 | 6/1994 | Orth et al. | 424/423 |
| 5,336,194 | 8/1994 | Polaschegg et al. | 604/175 |
| 5,350,360 | 9/1994 | Ensminger et al. | 604/93 |
| 5,360,407 | 11/1994 | Leonard | 604/175 |
| 5,399,168 | 3/1995 | Wadsworth, Jr. et al. | 604/175 |
| 5,443,497 | 8/1995 | Venbrux | 604/8 |

CATHETER WITH VALVE

This application is a continuation-in-part of application Ser. No. 08/183,151, now U.S. Pat. No. 5,562,617 filed on Jan. 18, 1994.

BACKGROUND OF THE INVENTION

1. The Field of Invention

The present invention relates to indwelling catheters used to access the body's circulation. More particularly, this invention provides a novel means for intermittent vascular access using an indwelling device in the general shape of a "T", in conjunction with a valve located within the lumen of the catheter, thereby reducing the thrombotic and hemodynamic consequences that accompany other available devices.

2. Related Art

The advent of hemodialysis for the treatment of End-stage Renal Disease has prompted the development of many vascular access devices for the purpose of acquiring large quantities of blood for passage through an extra-corporeal circuit during the hemodialysis procedure. Available devices have consisted of devices employing indwelling venous catheters or flow through shunt devices which create an artificial fistula between an artery and vein.

Current catheter technologies are limited by relatively poor flows and by their tendency to be irritative resulting in vessel stenosis, thrombosis, and occasionally vessel perforation. They frequently dysfunction for mechanical reasons related to the vessel wall, catheter positioning, or thrombus formation in the catheter lumen. Flow through shunt devices which create a fistulous connection between artery and vein have been the mainstay of modern vascular access for dialysis. These devices are likewise fraught with hazards. Installation of these "shunts" is an extensive surgical procedure resulting in significant tissue trauma and pain. Once in place, the shunts result in additional cardiac output needs with as much as one-fifth of the cardiac output (approximately 1000 ml per minute) required for adequate function. In addition, the transfer of the arterial pressure wave results in damage to the vein at the point of anastomosis with the shunt resulting in intimal hyperplasia and subsequent shunt occlusion or thrombosis. When this occurs, another vein segment must be used for shunt revision, and exhaustion of available sites is distressingly common. The expense both in terms of health care dollars and human misery is enormous. Repeated punctures of the wall of the shunt result in eventual failure and surgery to repair or replace the shunt.

Each of the available access technologies mentioned thus far are also complicated by the possibility of recirculation of blood already passed through the extra-corporeal circuit resulting in loss of treatment efficiency. The harm done to patients by the "recirculation syndrome" is insidious and at times undetected until great harm has been done.

Catheters which occupy only a portion of the vessel lumen are subject to movement within the vessel, which can cause irritation or even vessel perforation. Further, catheters which occupy only a portion of the vessel lumen, and which are inserted or threaded through the lumen for substantial distances tend to disrupt the normal flow of blood through the vascular structure, altering the hemodynamics of the blood flow in a manner which can damage the vessel, the components of the blood, and which can encourage thrombosis.

What is needed is an indwelling catheter that causes minimal disruption of blood flow through the lumen of the vascular structure during nonuse of the catheter, which does not cause vessel stenosis, thrombosis, or vessel perforation, which is capable of handling large quantities of blood, and which will retain its usefulness for a long period of time after implantation.

SUMMARY OF THE INVENTION

The indwelling catheter with valve of the present invention is shaped generally like a "T." The top of the "T" is placed in the lumen of a vascular structure. The catheter occupies the entire lumen of the vascular structure, such that all blood passing through the vascular structure must pass through the catheter. The leg of the "T" extends out of the wall of the vascular structure and is attached to an implanted port or percutaneous device. The leg of the "T" may extend from the implanted portion of the catheter at any angle, including a 90 degree angle, but it is preferred that the leg of the "T" extend from the implanted portion of the catheter in a direction which is toward the upstream or source of blood flow in the vascular structure. The angle formed between the leg of the "T" and the upstream end of the implanted portion of the catheter is an acute angle. The angle formed between the leg of the "T" and the downstream end of that portion of the catheter within the vascular structure is an obtuse angle. A preferred angle between the leg of the "T" and the upstream end of the implanted portion of the catheter is approximately 45 degrees. The result of this design is such that the forces which would otherwise tend to cause blood to flow into the leg of the "T" when the catheter is not in use are reduced. It is desirable to prevent blood from entering the leg of the "T" when the catheter is not in use, in order to avoid possible occlusion of the lumen of the catheter in the leg of the "T" due to thrombosis. Occlusion of that portion of the catheter which is within the vascular structure is not likely to occur, since blood flow is maintained through that portion of the catheter at all times.

As an additional means to prevent blood flow into the leg of the "T" of the catheter during nonuse, a valve is placed at the point where the leg of the "T" joins that portion of the catheter which lies within the vascular structure. During nonuse of the catheter, the valve closes in a manner which leaves the surface of the valve area consistent or flush with the inner surface of the portion of the catheter which lies within the lumen of the vascular structure. When the valve is closed, the implanted portion of the catheter is essentially a smooth tube which has minimal impact on blood flow through the vessel. A number of valves known in the prior art may be used, but the preferred valve is a slit valve placed directly in the side wall of the implanted portion of the catheter, or in a membrane that occupies the lumen of the leg of the "T", as close as possible to the point of connection to the implanted portion of the catheter. Depending upon the purpose for which the catheter is to be used, the valve may be unidirectional or bidirectional. In applications where fluid is only to be added or returned to the patient using the catheter, a unidirectional valve is preferred, since the opportunity for blood flow into the leg of the "T" when the catheter is not in use is further reduced.

Materials of construction well known in the art may be used for the manufacture of the catheter. However, it is important that that portion of the catheter which lies within the lumen of the vascular structure be particularly biocompatible with the vascular structure, since it is intended that the vascular structure in contact with the catheter remain viable. Since the catheter, unlike most prior art catheters, is not designed to be pushed or threaded some distance into a vascular structure, the catheter may be comprised of relatively rigid material. This may be accomplished by including a reinforcing spring within the catheter wall. The materials of construction are of sufficient rigidity to maintain the preferred angle between the leg of the "T" and that portion of the catheter within the lumen of the vascular structure.

Near the two ends of the implanted portion of the catheter are provided means to secure the catheter in place in the vascular structure. The outer circumference of the intravascular tubing is greater near the ends of the catheter, such that the vascular structure must stretch slightly to accommodate the catheter. Additionally, the intravascular tubing may have a series of outer ribs around its outer circumference which further prevent movement of the vessel relative to the catheter. Use of ribs or expanded outer circumference must not be such to prevent the long term viability of the vascular structure, but are sufficient to hold the catheter in place and prevent blood flow between the outer wall of the catheter and the vascular structure.

The instant invention enables one to access both the arterial and venous structures in a manner which does not cause vessel stenosis, thrombosis, or vessel perforation. Arterial and venous structures may be accessed separately, without fistulous communication, thus eliminating recirculation completely during hemodialysis and similar procedures, reducing dramatically the demands on the heart. Use of two of the catheters of the instant invention during hemodialysis, one inserted in an arterial structure and one inserted in a venous structure, avoids increased flow to the venous structures experienced using current dialysis technologies, and further avoids the arterial pressures which can be transmitted to the venous vascular wall. Installation of the invention requires no additional tissue disruption than use of existing catheter devices.

DETAILED DESCRIPTION OF THE PREFERRED EMBODIMENT

Figure 1:
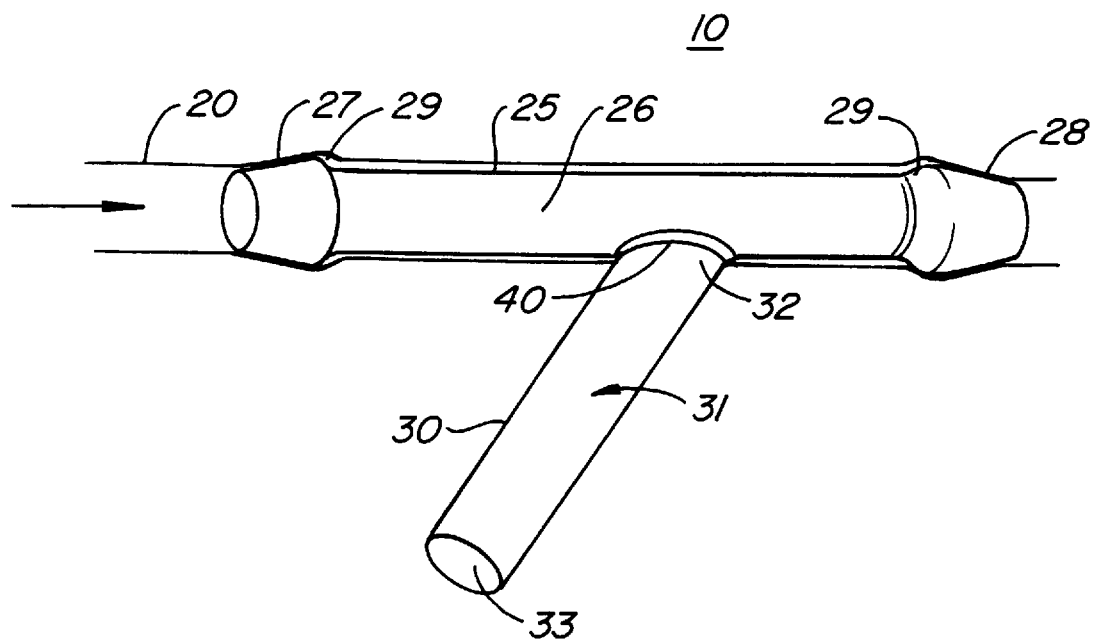
FIG. 1 shows a perspective view of the preferred embodiment of the present invention implanted within a vascular structure.

Referring to FIG. 1 there is depicted a catheter 10 of the present invention implanted within a vascular structure 20. The catheter is shaped generally like a "T" and is comprised of two primary sections; the intravascular tube 25 and the access leg 30. The intravascular tube 25 is an elongated tube having a single lumen 26, open on both ends. When implanted within a vascular structure 20, the intravascular tube 25 will have an upstream end 27, and a downstream end 28, determined by the direction of blood flow in the vascular structure 20. In FIG. 1 the direction of blood flow is indicated by the arrow within the vascular structure 20.

The access leg 30 is an elongated tube having a single lumen 31. The distal end 32 of the access leg 30 is connected to the intravascular tube 25, generally near the mid-point of the intravascular tube 25. The access leg 30 may extend from the intravascular tube 25 at any angle, including a 90 degree angle, but it is preferred that the access leg 30 of the catheter 10 extend from the intravascular tube 25 in a direction which is toward the upstream end 27 of the intravascular tube 25. The angle formed between the access leg 30 and the upstream end 27 of the intravascular tube 25 is an acute angle. The angle formed between the access leg 30 and the downstream end 28 of the intravascular tube 25 is an obtuse angle. A preferred angle between the access leg 30 and the upstream end 27 of the intravascular tube 25 is approximately 45 degrees.

Figure 3:
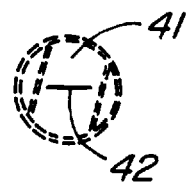
FIG. 3 shows a cross sectional view of the valve of the preferred embodiment of the present invention in the closed position.
Figure 4:
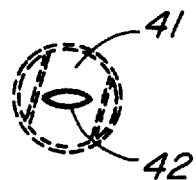
FIG. 4 shows a cross sectional view of the valve of the preferred embodiment of the present invention in the open position.
Figure 2:
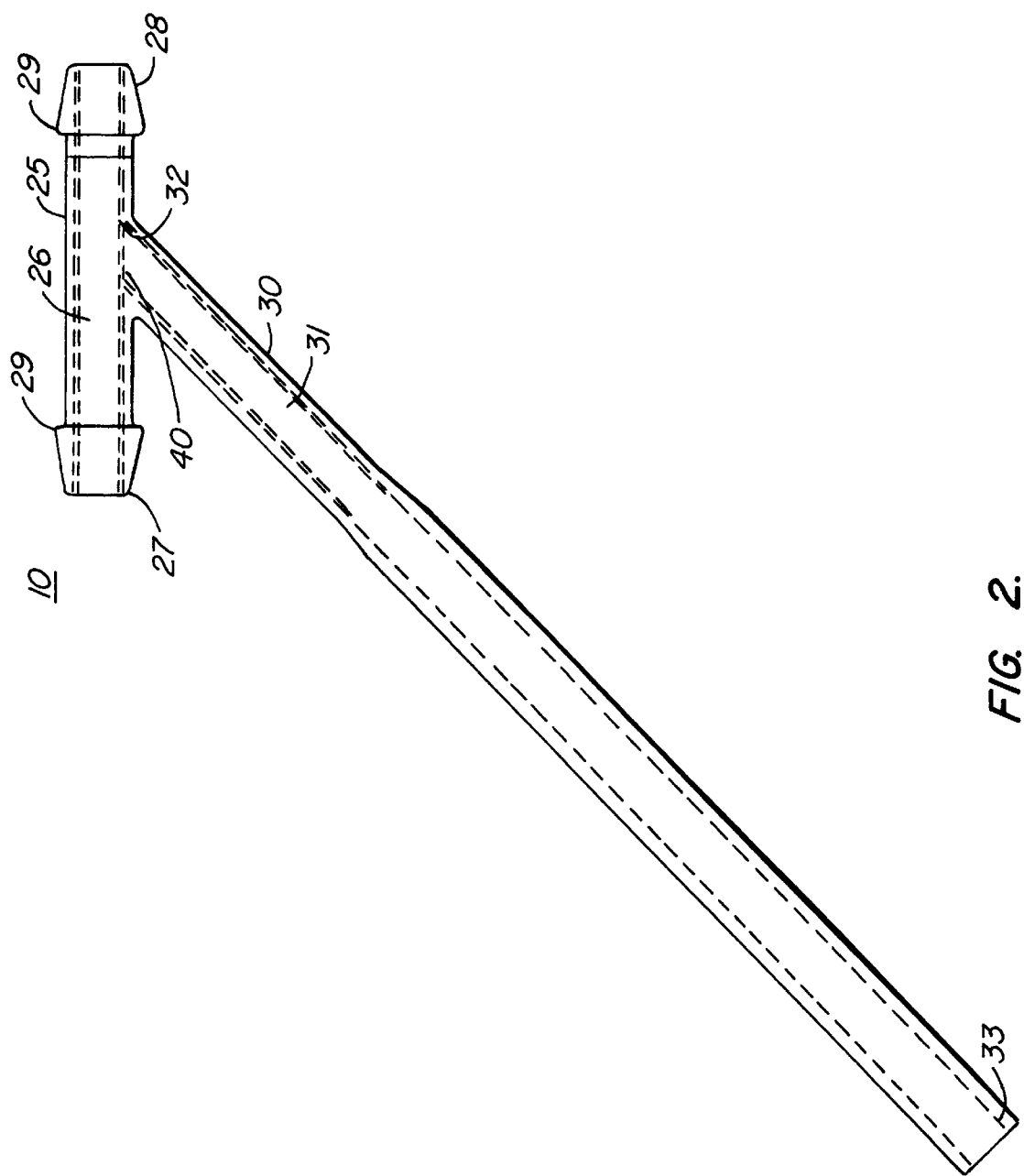
FIG. 2 shows a cross sectional view of the preferred embodiment of the present invention.

A valve 40 is located at the point of connection between the distal end 32 of the access leg 30 and the intravascular tube 25. The preferred valve 40 is a slit valve. Such valves are well known in the art. As best shown in FIG. 3, the slit valve is comprised of a membrane 41 which has a slit 42 extending partially across the membrane 41 and completely through the membrane 41. The membrane 41 acts to prevent fluid flow through the lumen 31 of the access leg 30, except when adequate differential pressure exists on opposite sides of the membrane 41 to cause the slit 42 to open, as is shown in FIG. 4. The membrane 41 is located such that the side of the membrane 41 located towards the vascular structure is essentially flush with the inner wall of the intravascular tube 25. When the catheter 10 is not in use, the membrane 41 of the valve 40 and the inner surface of the intravascular tube 25 form a continuous tube that has minimal impact on normal blood flow through the vascular structure.

In the preferred embodiment, the membrane 41 is comprised of a portion of the side wall of the intravascular tube 25. To create the valve 40, a slit 42 is cut in the side wall of the intravascular tube to correspond to the point of connection of the access leg 30. In this manner, when the valve is closed, the inner surface of the intravascular tube 25 is a continuous smooth surface which has minimal impact on normal blood flow. When the valve 40 opens, fluid flow between the lumen 31 of the access leg 30 and the lumen 26 of the intravascular tube 25 occurs.

The outer circumference of the intravascular tube 25 is provided with expanded caps 29 to hold the catheter 10 in place within the vascular structure 20. One each of these expanded caps 29 may be placed proximate the upstream end 27 and proximate the downstream end 28 of the intravascular tube 25. The expanded caps 29 have an enlarged outer circumference which tends to slightly stretch the wall of the vascular structure 20, providing a snug fit, but not preventing the continued viability of the wall of the vascular structure 20. Additional areas of expanded outer diameter (not shown) may be spaced along the outer surface of the intravascular tube 25. The fit between the wall of the vascular structure 20 and the intravascular tube 25 must be of sufficient tightness to prevent passage of blood between the wall of the vascular structure 20 and the outer surface of the intravascular tube 25. All blood flowing through the vascular structure 20 should pass through the lumen 26 of the intravascular tube 25.

In use, the proximal end 33 of the access leg 30 of the catheter 10 may be connected to a subcutaneous port, or may extend percutaneously. The catheter 10 is suitable for use with any device requiring or facilitating intermittent vascular access. The catheter 10 of the present invention is particularly useful in hemodialysis, since such treatment requires large quantity blood flow, and requires relatively frequent vascular access over a long period of time. For such use two catheters 10 may be surgically implanted. One of the devices is implanted in an artery. The other device is implanted in a vein. In this manner both the venous and arterial circulations are accessed separately, without fistulous communication. Current use of shunts, which create a fistulous connection between artery and vein, not only involve a more extensive surgical procedure, but are fraught with problems including increased cardiac output requirements, damage to the vein due to arterial pressure waves, and frequent shunt occlusion or thrombosis. During hemodialysis, blood is removed from the catheter 10 implanted in an artery and is subjected to the extra-corporeal dialysis circuit. Removal occurs by reducing the pressure in the access leg 30 of the catheter 10, until the slit valve 40 opens, and blood flows from the intravascular tube 25 into the access leg 30. The treated blood is returned to the catheter 10 implanted in a vein. The increased pressure in the access leg 30 of this catheter causes the valve 40 to open, allowing blood to flow from the access leg 30 to the intravascular tube 25. Note that the valve 40 in the catheter 10 implanted in a vein may be unidirectional, such that blood is prevented from flowing past the valve 40 from the intravascular tube 25 to the access leg 30, even if the pressure in the intravascular tube 25 should exceed the pressure in the access leg 30. At the completion of the dialysis treatment the access legs 30 of both catheters 10 are filled with anti-coagulant fluid, to discourage occlusion of the access legs 30. A similar process may be used for apheresis or exchange transfusion procedures. Additionally, a single catheter 10 may be used for frequent administration of medication into artery or vein, or for large volume fluid infusions.

Surgical implantation of the catheter 10 is a straight forward procedure. The chosen artery or vein is located and isolated, and a small incision is made in the vascular structure 20. The intravascular tube 25 of the catheter 10 is inserted into the incision, with the access leg 30 extending out of the vascular structure 20 through the incision. The incision is then sutured to provide a snug fit around the access leg 30. The proximal end 33 of access leg 30 of the catheter 10 is then attached to a subcutaneous port or other device requiring intermittent vascular access.

Materials of construction well known in the art may be used for the manufacture of the catheter 10. However, it is important that the intravascular tube 25 be particularly biocompatible with the vascular structure 20, since it is intended that the vascular structure 20 in contact with the catheter 10 remain viable. Since the catheter 10, unlike most prior art catheters, is not designed to be pushed or threaded some distance into a vascular structure 20, the catheter may be comprised of relatively rigid material. This may be accomplished by including a reinforcing spring within the walls of the catheter 10. The materials of construction are of sufficient rigidity to maintain the preferred angle between the access leg 30 and the intravascular tube 25. Construction materials may be a spring wire reinforced silicone rubber, or other suitable materials well known in the art. The dimensions of the catheter 10 depend upon the size of the vascular structure 20 to be accessed. Typically the outer diameter of the intravascular tube 25 will be between 3 and 6 millimeters, with a wall thickness of approximately 1 millimeter, yielding a lumen 26 diameter of between 1 and 4 millimeters. A typical length of the intravascular tube 25 from upstream end 27 to downstream end 28 is between 20 and 50 millimeters. The maximum diameter of the outer surface of the expanded caps 29 is approximately 30 percent greater than the diameter of the intravascular tube 25 where no expanded cap 29 is present. The length and flexibility of the access leg 30 can vary depending upon the use of the catheter 10. For use with subcutaneous ports an access leg 30 length of approximately 100 millimeters is generally sufficient.

It is intended that the foregoing detailed description be regarded as illustrative rather than limiting and that it is understood that the following claims including all equivalents are intended to define the scope of the invention.

We claim:

1. A catheter with a valve for implantation in a vascular structure, said catheter comprising:
    an intravascular tube adapted to be implanted in a lumen of a blood vessel, said intravascular tube having an outer side wall and a lumen bounded by an inner wall therethrough;
    a flexible access leg having a distal end connected to the outer side wall of the intravascular tube and having a lumen therethrough which is fluidly coupled to the lumen of the intravascular tube; and
    a valve disposed at the distal end of the access leg, wherein the valve is flush with the inner wall of the lumen of the intravascular tube and wherein said valve opens in response to differential pressure.

2. A catheter as in claim 1, wherein the valve is a slit valve formed in the intravascular tube so that the slit valve is flush with the inner wall of the intravascular tube.

3. A catheter as in claim 2, wherein the slit valve is oriented in a direction parallel to the lumen of the intravascular tube.

4. A catheter as in claim 1, wherein the access leg is disposed at an inclined angle relative to the lumen of the intravascular tube.

5. A catheter as in claim 4, wherein the inclined angle is 45°.

6. A catheter as in claim 1, wherein the intravascular tube has a length in the range from 20 mm to 50 mm, and outer diameter in the range from 3 mm to 6 mm, and a lumenal diameter in the range from 1 mm to 4 mm.

7. A catheter as in claim 6, wherein the access tube has a length of approximately 100 mm.

8. A catheter as in claim 1, wherein the valve is bidirectional.

9. A catheter as in claim 1, wherein the valve is a slit valve.

10. A catheter as in claim 1, wherein the intravascular tube has an expanded cap at at least one end thereof.

11. A catheter as in claim 1, wherein the intravascular tube and access leg are composed of wire-reinforced silicone rubber.

12. A catheter with a valve for implantation in a vascular structure, said catheter comprising:
    an intravascular tube adapted to be implanted in a lumen of a blood vessel, said intravascular tube having an outer side wall and a lumen bounded by an inner wall therethrough;
    a bidirectional flexible access leg having a distal end connected to the outer side wall of the intravascular tube and having a lumen therethrough which is fluidly coupled to the lumen of the intravascular tube; and
    a valve disposed at the distal end of the access leg, wherein said valve opens in response to a differential pressure.

13. A catheter as in claim 12, wherein the valve is a slit valve formed in the intravascular tube so that the slit valve is flush with the inner wall of the intravascular tube.

14. A catheter as in claim 13, wherein the slit valve is oriented in a direction parallel to the lumen of the intravascular tube.

15. A catheter as in claim 12, wherein the access leg is disposed at an inclined angle relative to the lumen of the intravascular tube.

16. A catheter as in claim 15, wherein the inclined angle is 45°.

17. A catheter as in claim 12, wherein the intravascular tube has a length in the range from 20 mm to 50 mm, and outer diameter in the range from 3 mm to 6 mm, and a lumenal diameter in the range from 1 mm to 4 mm.

18. A catheter as in claim 17, wherein the access tube has a length of approximately 100 mm.

19. A catheter as in claim 12, wherein the valve is flush with the inner wall of the lumen of the intravascular tube.

20. A catheter as in claim 12, wherein the valve is a slit valve.

21. A catheter as in claim 12, wherein the intravascular tube has an expanded cap at at least one end thereof.

22. A catheter as in claim 12, wherein the intravascular tube and access leg are composed of wire-reinforced silicone rubber.

* * * * *